(12) United States Patent
Jessop et al.

(10) Patent No.: US 6,269,148 B1
(45) Date of Patent: Jul. 31, 2001

(54) RADIOGRAPHIC IMAGE MARKING SYSTEM

(75) Inventors: David W. Jessop; Wayne G. Jessop; Danielle E. Earl; C. Allen Newbury, all of Simi Valley, CA (US)

(73) Assignee: The Suremark Company, Minden, NV (US)

(*) Notice: Subject to any disclaimer, the term of this patent is extended or adjusted under 35 U.S.C. 154(b) by 0 days.

(21) Appl. No.: 09/188,475

(22) Filed: Nov. 9, 1998

(51) Int. Cl.[7] ....................................................... H05G 1/28
(52) U.S. Cl. ............................................. 378/162; 378/163
(58) Field of Search ..................................... 378/162, 163, 378/164, 165, 204, 207, 208

(56) References Cited

U.S. PATENT DOCUMENTS 4,860,331 * 8/1989 Williams et al. ..................... 378/163
5,383,233    1/1995 Russell .
5,469,847 * 11/1995 Zinreich et al. ..................... 378/163
5,706,324 * 1/1998 Wiesent et al. ..................... 378/163

* cited by examiner

*Primary Examiner*—David P. Porta
(74) *Attorney, Agent, or Firm*—Thorpe North & Western, LLP

(57) ABSTRACT

An radiographic marker system includes a structure creating a layer substantially transparent to imaging radiation at energies used in radiographic imaging applications where the marker is used, the layer being formed in an enveloping shape and having a thickness extent, and a radiopaque marker opaque to imaging radiation at energies used in radiographic imaging applications where the marker is used, the radiopaque marker being carried by the structure creating a layer transparent to imaging radiation, the system can further comprise an adhesive layer on a bottom surface of the structure creating a layer substantially transparent to imaging radiation, the adhesive facilitating placement and removal of the marker.

20 Claims, 2 Drawing Sheets

RADIOGRAPHIC IMAGE MARKING SYSTEM

BACKGROUND

1. Field of the Invention

This invention relates generally to radiographic imaging. More particularly, the invention relates to a radiographic image marking system for identifying and more clearly imaging certain protruding anatomical features in radiographic imaging applications where the anatomy of interest is at least partially compressed in making the image.

2. Description of Related Art

It has been recognized that there is often a need to mark certain anatomical structure in radiographic imaging applications for the convenience of medical personnel interpreting the images and to reduce the probability of uncertainty, confusion, or mistake concerning the nature of the anatomical structure. This is true for example in mammography, where the breast is compressed and certain features, particularly moles and the like for example, protrude from the surrounding skin of the patient. It is known that structure which protrudes from the surrounding epithelium, such as moles for example, can produce artifactal images which may be confused with internal structural abnormalities. In such applications an image susceptible to misinterpretation may result.

In the past such structure was identified and marked with radiopaque markers such as solder wire or lead shot taped to the skin, or later marker labels incorporating radiopaque markers made of coated lead or bismuth for example attached to an adhesive base for securing the marker temporarily to the skin of the patient. It has been recognized that it is desirable in addition to marking the location of the protruding structure to provide for more clear imaging of the structure itself. To this end a marker ring comprising a torroidal marker formed of a material partially opaque to imaging radiation, such as a rubber material for example, has been used. The ring marks the location of the structure of interest and also prevents the structure from being entirely compressed, for example in mammography applications in which the breast is compressed during the imaging process. This produces an image of the structure as well as the marker ring as disclosed and described for example in U.S. Pat. No. 5,383,233 issued to Donald G. Russell Jan. 17, 1995.

While the marking system disclosed in the Russell '233 patent allows improved imaging of the structure marked, certain limitations inherent in this system have been recognized. In order to prevent compression of the anatomical structure marked the marker must have a thickness associated with it. Variation of thickness of known markers of this type produces variation in the amount of material used and commensurately variation in the amount of radiation absorbed by the marker. Accordingly the image produced will show detail underneath the marker to a greater or lesser extent depending on the thickness of the marker. As can be appreciated anatomical structure that protrudes farther from the outer surface of the skin would require a thicker marker ring, and accordingly more radiation would be absorbed and the resulting image would show the structure underneath the marker more obscured. In practical application of the known system the protruding structure can be compressed to a more or less extent and markers of a rather more consistent thickness are employed.

What is recognized as needed, and has heretofore not been available, is a marking system which is consistent in producing an image of the protruding structure and the accompanying marker and mitigates the problems of compression of the protruding structure and provides the desired advantages mentioned. The present invention is directed to fulfilling this need.

SUMMARY

Briefly, and in general terms, the present invention accordingly provides a radiographic marker system comprising: a) a substantially radiotranslucent structure creating a layer substantially transparent to imaging radiation at energies used in radiographic imaging applications where the marker is used, the layer being formed in an enveloping shape and having a thickness extent; and b) a radiopaque marker opaque to imaging radiation at energies used in radiographic imaging applications where the marker is used, the radiopaque marker being carried by the structure creating a layer transparent to imaging radiation. The image marking system can further comprise an adhesive disposed beneath and attached to the structure, the adhesive facilitating attachment of the structure adjacent anatomical structure to be marked.

These and other aspects and advantages of the invention will become apparent from the following detailed description, and the accompanying drawing figures, which illustrate by way of example the features of the invention.

DESCRIPTION

Figure 1:
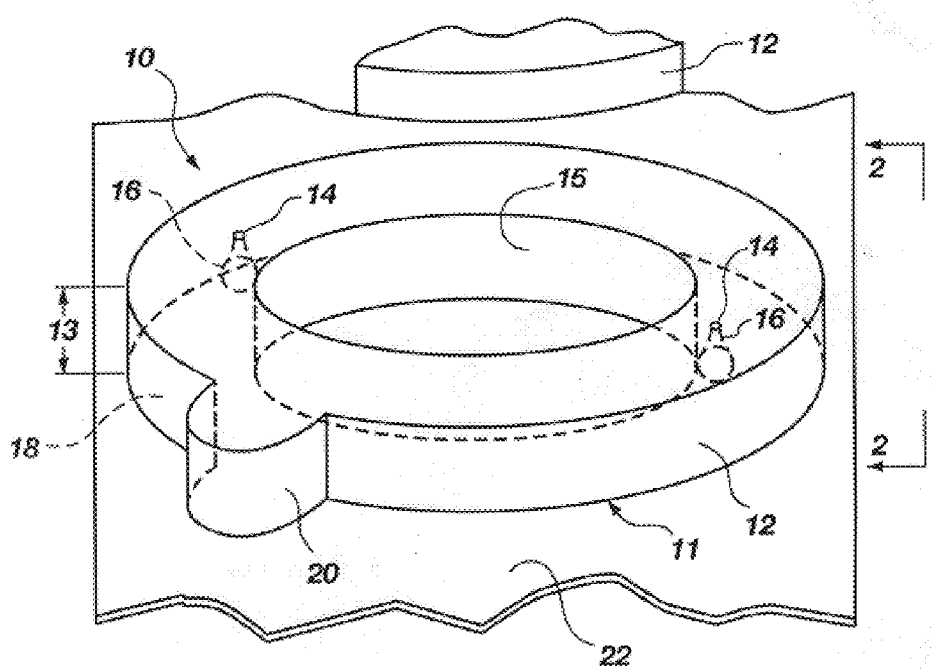
FIG. 1 of the drawings is a perspective view of a marking system in accordance with the invention.

As shown in FIG. 1 for purposes of illustration, a marker system 10 in accordance with the invention comprises a foam ring 12 having a thickness extent 13 which serves to surround and preserve a protruding structure such as a nevoid protrusion, for example, in radiographic imaging applications where such a protruding structure would otherwise be flattened. The foam ring comprises a structure which creates a radiolucent layer through which imaging radiation passes without casting a discernable shadow on an image plate where a radiographic image is created. The foam ring further comprises two perforations 14 into each of which a marker ball 16 formed of a radiopaque material is inserted, and a central opening 15 defined by the foam ring. The foam ring is formed of a foamed elastomer and the marker balls are retained in the perforations by rebound forces exerted by the surrounding foam. The foam ring has an adhesive coated surface 18 on the bottom side for attachment to the epithelium of the patient. The marker balls are accordingly held adjacent the protruding structure being marked; and at the same time the protruding structure is protected from being flattened by support provided to surrounding tissue of the patient by the foam ring comprising a layer of radiolucent material in an enveloping shape. As can be appreciated the marker can also be used in other radiographic imaging applications besides mammography, and can be used to mark other structure, such as nipples, scar tissue, wounds, and palpable masses for example.

The foam ring 12 further comprises a lifting tab 20 which extends radially outward from the ring and facilitates grasping the ring for handing and application and removal of the marker to and from the patient's anatomy. The marking system 10 can include a base tape 22 formed for example of paper coated with a silicone release agent, the foam ring being initially mounted on the base tape. The adhesive coated surface 18 releases from the base tape when the foam ring and the base tape are separated by peeling one from the other in dispensing the marker system 10 for use. Further, a multiplicity of foam rings can be disposed on the base tape and dispensed consecutively therefrom. As can be appreciated this facilitates convenient storage of numerous markers on a roll of base tape for example, allowing convenient dispensing from a box containing a roll of base tape with markers thereon for example.

Figure 2:
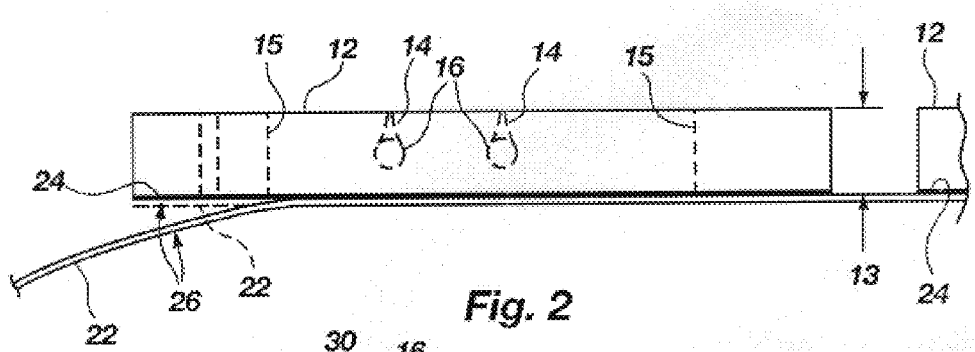
FIG. 2 of the drawings is a side elevation view of the marker system shown in FIG. 1 taken along line 2—2 in FIG. 1.

With reference to FIG. 2, in one embodiment the marking system 10 includes as illustrated for example a base layer 24 comprising a polyethylene film. The film is coated with adhesive on both sides. One side is attached to the foam ring 12 and the other initially to the base tape 22. The side adhering initially to the base tape comprises the adhesive surface 18 which adheres to the patient's anatomy when the marker is dispensed from the base tape and placed on the patient. The adhesive on the adhesive surface contacting the patient is a non-sensitizing acrylic pressure-sensitive adhesive such as MED 6000 adhesive available from Avery-Dennison Corp. of Pasadena Calif., adapted and approved for human use. The adhesive can be neutralized in a bottom area 26 below the lifting tab, allowing the lifting tab to be more easily lifted for removal of the marker 10 from the base tape 22 or the skin for example of a patient. In an alternative embodiment the basetape is undercut in the area under the lifting tab so that the basetape is lifted with the marker in the area 26 under the lifting tab only, covering the adhesive in that area to facilitate lifting the marker from the base tape or a patient's anatomy.

The foam from which the foam ring 12 is formed is selected so as to minimize absorption of imaging radiation, while at the same time providing a layer having a thickness extent 13 which resists compression. In this way the shape of the protruding anatomical structure being marked is preserved at least insofar as it does not extend beyond the thickness extent of the supporting layer. The foam ring, as can be appreciated, need not necessarily be circular in shape, or indeed be a complete circle. Other shapes (not shown) such as square, triangular, oval, pentagonal, hexagonal, etc. can be used, and can serve a further function of identifying the particular type of marker as will be discussed below. Moreover, C-shaped foam can be used for example. In another embodiment pillars of foam disposed for example on a thin radiopaque base of enveloping shape could also be used to create the layer having a thickness extent which is translucent to imaging radiation. Marker elements such as the marker balls 16 shown can be imbedded in foam creating such a layer and, as can be appreciated, latitude in placement of the marker balls within the foam also allows for variation in the pattern of the marker ball placement also.

The foam used in the illustrated embodiment is a physically blown nitrogen-expanded closed-cell foam of polyethylene copolymer resin such as LD45 foam available commercially from Zotefoam, Inc. of Hackettstown, N.J. However, great variation in the properties of the foam is possible; depending for example on the stiffness desired, better preserving the shape of the protruding structure, or compliance desired, for example to increase comfort to the patient. Foam is chosen because of its very low density, as it is desirable to make the layer having a thickness extent transparent insofar as possible to imaging radiation at energy levels used in radiographic imaging. This is so that internal anatomical features of interest will not be obscured by the marker 10 except at the points, relatively quite small in cross-sectional area, where the radiopaque markers 16 are located. In another embodiment, for example, a closed cell foam of cross linked polyolefin, marketed under the brand name VOLARA by the Voltek division of Sekisui American Corp. of Lawrence, Mass. is used to form the foam ring 12 comprising the radiolucent layer having a thickness extent.

Figure 3:
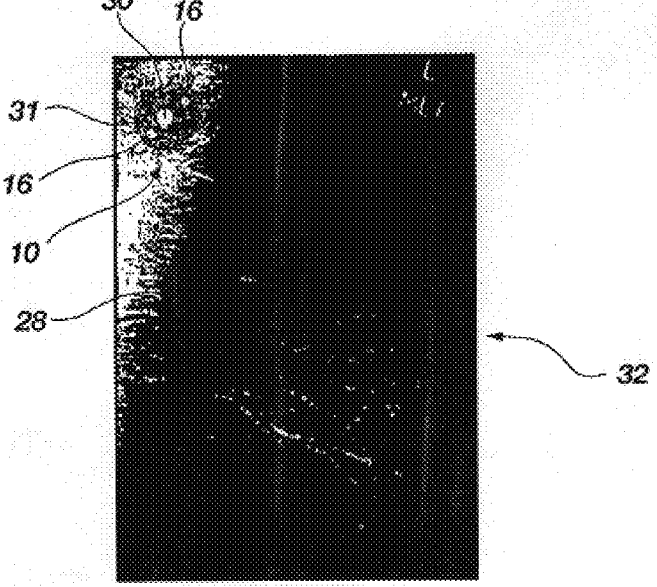
FIG. 3 of the drawings is a copy of a radiographic image produced using a marker system of the invention FIG. 4 of the drawings is a top view of the marker shown in FIGS. 1 & 2.

With reference to FIG. 3 as can be appreciated by those skilled in the art in mammographic applications where tissue 28 of the breast is compliant the resulting radiographic image 32 when the marking system 10 of the invention is used includes: an image of the two markers 16 comprising radiopaque balls formed of lead, bismuth, or other substance which readily absorbs imaging radiation; the protruding nevus 30 or other protruding anatomical structure of interest marked, which appears slightly lighter due to a longer path for imaging radiation through the tissue comprising the protruding structure; and a slightly darker area 31 surrounding the protruding structure, which may also be slightly darker than surrounding areas outside the extent of the foam ring, occasioned by a shorter path for imaging radiation through the surrounding tissue due to the presence of the enveloping layer of radiolucent material having a thickness extent comprising in the illustrated embodiment the foam ring (which does not produce an image, and is not shown). Nevertheless, the foam is chosen so that structure under the marker 10 is not obscured by the foam ring comprising the radiolucent layer at energy levels used in radiographic imaging.

Figure 9:
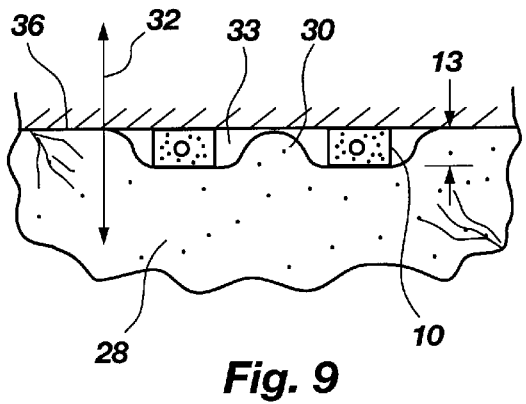
FIG. 9 of the drawings is a perspective view of a marker comprising another embodiment of the invention.

This can be appreciated also with reference to FIG. 9 which shows the marker system 10 attached to a patient's anatomy 28 surrounding a protruding anatomical structure 30. The direction of travel 32 of imaging radiation is orthogonal to a radiolucent layer 33 having a thickness extent 13 surrounding the protruding anatomical structure and also to a surface 36 compressing the patient's anatomy and the radiographic imaging film (not shown).

With reference again to FIGS. 1 & 2, the marker system illustrated by way of example is formed by applying a layer of foam having a thickness extent 13 to the base film 24 having adhesive on both sides. The base film is already attached to the underlying silicone coated paper comprising the base tape 22. The foam ring and base film are then die-cut to the desired shape shown. The die also is configured to make the perforations 14 which receive the markers 16. The foam surrounding the foam ring 12 as well as the foam within the central opening 15 is removed, the base film underlying the foam being removed with the foam as the adhesive on the underside of the base layer relatively easily releases from the silicone-coated base tape. The perforated foam ring remains on the base tape. As mentioned the lifting tab 20 can be made to not stick to the base tape 22 by under-cutting the base tape around the area 26 beneath the lifting tab 20 portion or applying a neutralizing agent to the area. The perforations 14 can also be made by separate process step. The markers comprising marker balls 16 are inserted into the perforations 14 sufficiently deeply that foam closes over them, thereby retaining them in the foam. The balls can be coated with adhesive prior to insertion in another embodiment.

Figure 4:
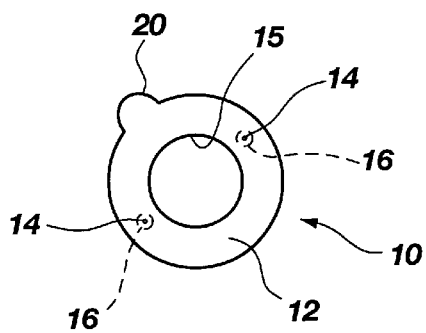

As shown in FIG. 4 the pattern of marker ball 16 placement in one embodiment is two balls placed in line across the central opening 15 in the foam ring 12. One ball could be used but this can introduce ambiguity into interpretation of the resulting image as the structure of interest may conceivably appear adjacent the marker ball in any direction in the resulting image. Using two balls gives a resulting image where reviewing medical personnel will know that the marked anatomical structure is between the two small dots.

Figure 5:
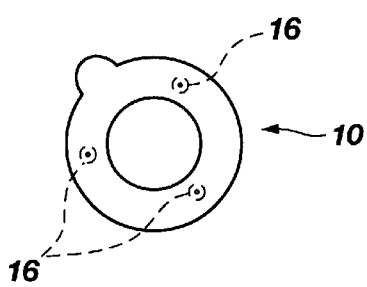
FIG. 5 of the drawings is a top view of a marker comprising another embodiment of the invention.
Figure 6:
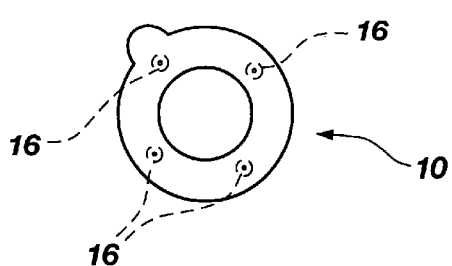
FIG. 6 of the drawings is a top view of a marker comprising another embodiment of the invention.

As can be seen in FIGS. 5 and 6, patterns of three marker balls 16 and four marker balls, respectively, can be employed. The pattern of balls can be used to provide additional information to medical personnel. For example, different patterns can be used to indicate different types of protruding structure. Consequently identification of the location and nature of the protruding structure, as well as more clearly imaging that structure is facilitated by the marking system of the invention.

Figure 7:
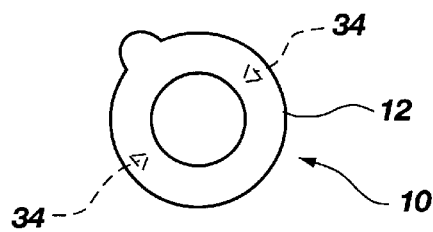
FIG. 7 of the drawings is a top view of a marker comprising another embodiment of the invention.

With reference to FIG. 7, radiopaque markers 34 can be formed in other shapes besides the spheroidal shape of the marker balls (16 in FIG. 6) shown in the preceding figures. For example other embodiments can include markers 34 formed in the shape of a triangle inserted in triangular shaped die-cut holes in the foam. Alternatively shaped die-cut holes in the foam can be filled with a mixture of an adhesive binder and powdered radiopaque material such as bismuth. The hardened mixture will be formed and will be contained in the shape of the hole by the closed-cell foam. Because of the thickness extent of the foam ring 12, materials less absorbing of imaging radiation can also be used as a marker if disposed substantially through the thickness extent of the radiolucent layer comprising the foam ring 12. For example if the triangular markers 34 shown were formed of a dense polymeric resin contained in triangular die-cut holes as shown they would present end-on to imaging radiation directed orthogonally to the radiolucent layer formed by the foam ring and would be radiopaque due to the large distance the imaging radiation would have to travel through them.

Figure 8:
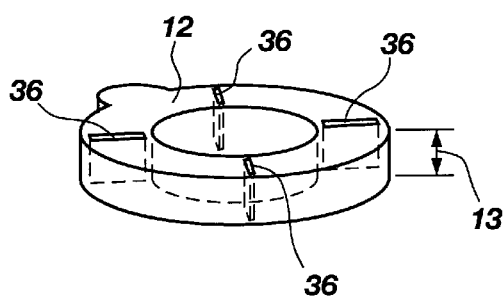
FIG. 8 is a side elevation view partly in cross section of a marker according to the invention in use.

In another embodiment shown in FIG. 8 the radiopaque markers 36 comprise four plates of relatively denser material inserted in crossed linear die-cuts through the foam ring 12. Again, the plates present end-on to imaging radiation and due to their thickness extent 13 they are opaque to imaging radiation at normal energy levels. As can be appreciated such markers would result in crossing-oriented lines of undeveloped plate and hence such a crossed line pattern in the resulting image, the protruding structure of interest being at the imaginary intersection of the crossed lines of the pattern. Otherwise the marking system shown in FIG. 8 is as before described.

With reference to FIG. 9 the radiolucent layer 33 having a thickness extent 13 maintained around the protruding structure 30 allows the protruding structure to be imaged, but also allows underlying tissue features, such as microcalcifications to be imaged. This is due to the fact that absorption of imaging radiation is minimal in the foam ring 12 due to its low density. As mentioned, The foam ring is transparent to imaging radiation at energy levels customarily used in radiographic imaging. In another embodiment shown in FIG. 10 the foam ring is replaced by an injection molded support structure 38 which is radiolucent but for marker portions 40 which present endwise to imaging radiation and are radiopaque due to the effective thickness of material imaging radiation must traverse. The marker portions also function to maintain the thickness extent 13 of a radiolucent layer formed by the support structure. A polymeric resin having a density chosen so that the marker portions are radiopaque and the rest of the structure comprising a thin plate 41 is radiolucent is used to form the marking system 10.

In the embodiment shown the layer of radiolucent material is mostly air, created as the support structure prevents tissue comprising the protruding structure 30 from being compressed. Adhesive is disposed on a bottom surface 42 of the marker system 10. The image produced by the marking system shown is similar to that of the embodiment shown in FIG. 8.

Figure 10:
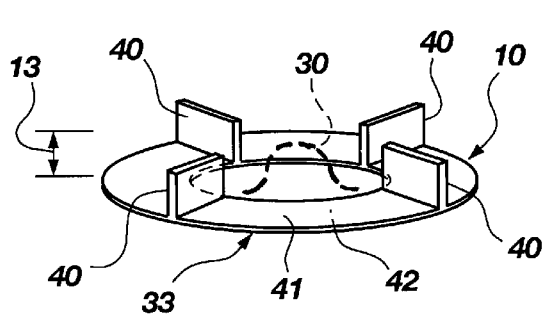
FIGS. 10 and 11 of the drawings are perspective views of a marker comprising another embodiment of the invention.
Figure 11:
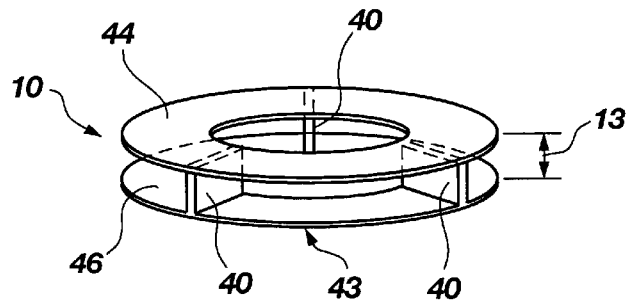

With reference to FIG. 11 in another embodiment the radio translucent layer having a thickness extent 13 is formed by a structure 43 similar to that shown in FIG. 10 further comprising a very thin top plate 44 in addition to a very thin bottom plate 46. Marker portions 40 also function to maintain separation of the top and bottom plates and thus the thickness extent of the radiolucent layer formed by the structure. This embodiment is also injection molded from a polymeric resin chosen so as to provide radiolucent and radiopaque portions as described above, the marker portions producing a marker shadow image of three lines extending radially outward from the protruding structure marked.

As can be appreciated the marking system in accordance with the invention provides an marked image of anatomical structure of interest, particularly that which protrudes from the epithelium. The marking system is simple and can be produced at low cost. The marking system further provides an indication function while enhancing the imaging of protruding structure of interest. Finally, the marking system allows interior anatomical structures to be imaged through the radiolucent layer formed by the marking system. It will be apparent from the foregoing that while a particular form of the invention has been illustrated and described, various modifications can be made without departing from the spirit and scope of the invention. Accordingly, it is not intended that the scope of the invention be limited, except by the appended claims.

What is claimed is:

1. A radiographic marker system, comprising:
   a. a radiolucent base layer comprising an adhesive, said base layer formed in an enveloping shape, adapted to retain a marker adjacent structure to be imaged;
   b. a structure creating a layer of material substantially transparent to imaging radiation at energies used in radiographic imaging applications where the marker is used, the layer being formed in an enveloping shape and having a thickness extent;
   c. an imaging radiation absorbent marker opaque to imaging radiation at energies used in radiographic imaging applications where the marker is used, the imaging radiation absorbent marker being carried by the structure creating a layer of material transparent to imaging radiation said marker being configured to be substantially smaller in cross-sectional area presented to imagining radiation than that of said layer.

2. The radiographic marker system of claim 1, wherein the structure creating a layer of material substantially transparent to imaging radiation comprises a foam of polymeric resin.

3. The radiographic marker system of claim 2, wherein the foam is a closed-cell foam.

4. The radiographic marker system of claim 1, wherein the layer substantially transparent to imaging radiation is formed in a ring adapted to surround the structure to be imaged.

5. The radiographic marker system of claim 1, wherein the imaging radiation absorbent marker is embedded in the structure creating a layer of material substantially transparent to radiographic imaging radiation.

6. The radiographic marker system of claim 5, where the imaging radiation absorbing marker comprises a ball formed of radiopaque material.

7. The radiographic marker system of claim 2, where the layer of material substantially transparent to imaging radiation further comprises a perforation, and the imaging radiation absorbing marker is inserted into the perforation and is retained therein by the material comprising the layer of material substantially transparent to imaging radiation.

8. The radiographic marker system, of claim 1, wherein the marker system comprises a plurality of radiopaque markers.

9. The radiographic marker system of claim 8, wherein the markers are arranged in a pattern.

10. The radiographic marker system of claim 9, wherein the pattern comprises an indica of a property of an anatomical feature marked.

11. The radiographic marker system of claim 1, further comprising an adhesive releasable base layer from which the structure is dispensed.

12. A radiographic marker system comprising:
   a. a structure creating a layer substantially transparent to imaging radiation at energies used in radiographic imaging applications where the marker is used, the layer being formed in an enveloping shape as seen by the imaging radiation and having a thickness extent;
   b. A radiopaque marker opaque to imaging radiation at energies used in radiographic imaging applications where the marker is used, the radiopaque marker being carried by the structure creating a layer transparent to imaging radiation, said marker being configured to be substantially smaller in cross-sectional area presented to imaging radiation than that of said layer.

13. The radiographic marker system of claim 12, wherein the structure comprises a polymeric resin.

14. The radiographic marker system of claim 13, wherein the polymeric resin is elastomeric.

15. The radiographic marker system of claim 13, wherein the polymeric resin is foamed.

16. The radiographic marker system of claim 13, comprising a plurality of radiopaque markers.

17. The radiographic marker system of claim 16, wherein the radiopaque markers are arranged in a pattern.

18. The radiographic marker system of claim 16, further comprising a lifting tab facilitating handling of the marking system.

19. The radiographic marker system of claim 12, further comprising a polymeric film layer disposed beneath and attached to the structure, the polymeric film layer carrying an adhesive facilitating attachment of the structure adjacent anatomical structure to be marked.

20. A radiographic marker system comprising:
   a. a structure creating a layer substantially transparent to imaging radiation at energies used in radiographic imaging applications where the marker is used, the layer being formed in an enveloping shape and having a thickness extent;
   b. A radiopaque marker opaque to imaging radiation at energies used in radiographic imaging applications where the marker is used, the radiopaque marker being carried by the structure creating a layer transparent to imaging radiation, said marker being configured to be substantially smaller in cross-sectional area presented to imaging radiation than that of said layer;
   c. an adhesive disposed beneath and attached to the structure, the adhesive facilitating attachment of the structure adjacent anatomical structure to be marked.

* * * * *